(12) United States Patent
Martin

(10) Patent No.: US 9,481,613 B2
(45) Date of Patent: *Nov. 1, 2016

(54) LIQUID-FERTILIZER READY FORMULATIONS OF BIFENTHRIN

(71) Applicant: FMC Corporation, Philadelphia, PA (US)

(72) Inventor: Timothy M. Martin, Ringoes, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/597,427

(22) Filed: Jan. 15, 2015

(65) Prior Publication Data

US 2015/0158782 A1 Jun. 11, 2015

Related U.S. Application Data

(62) Division of application No. 14/217,640, filed on Mar. 18, 2014, now Pat. No. 8,937,054.

(60) Provisional application No. 61/912,259, filed on Dec. 5, 2013.

(51) Int. Cl.
| | | |
|---|---|---|
| A61K 31/695 | (2006.01) | |
| A01N 53/00 | (2006.01) | |
| C05G 3/02 | (2006.01) | |
| A01N 25/10 | (2006.01) | |

(52) U.S. Cl.
CPC ............... *C05G 3/02* (2013.01); *A01N 25/10* (2013.01); *A01N 53/00* (2013.01)

(58) Field of Classification Search
None
See application file for complete search history.

(56) References Cited

U.S. PATENT DOCUMENTS

| | | | |
|---|---|---|---|
| 3,060,084 A | 10/1962 | Littler | |
| 4,360,376 A | 11/1982 | Koestler | |
| 5,583,090 A | 12/1996 | Stern et al. | |
| 5,834,006 A | 11/1998 | Smith et al. | |
| 5,925,464 A | 7/1999 | Mulqueen et al. | |
| 7,094,592 B2 | 8/2006 | Watanabe et al. | |
| 8,029,827 B2 | 10/2011 | Martin | |
| 8,263,527 B2 | 9/2012 | Martin | |
| 8,293,733 B2 | 10/2012 | Casana Giner et al. | |
| 8,524,222 B2 | 9/2013 | Jacobsen et al. | |
| 8,937,054 B1 * | 1/2015 | Martin | 514/63 |
| 8,993,484 B1 | 3/2015 | Martin et al. | |
| 2002/0115565 A1 | 8/2002 | Asrar et al. | |
| 2004/0023802 A1 | 2/2004 | Asrar et al. | |
| 2006/0166898 A1 | 7/2006 | Chen | |
| 2007/0135506 A1 | 6/2007 | Zeun et al. | |
| 2008/0206361 A1 | 8/2008 | Martin | |
| 2008/0306026 A1 | 12/2008 | Shirley | |
| 2009/0203746 A1 * | 8/2009 | Jadhav et al. | 514/341 |
| 2010/0016392 A1 * | 1/2010 | Kabanov et al. | 514/384 |
| 2010/0179198 A1 | 7/2010 | Mertoglu et al. | |
| 2010/0234225 A1 | 9/2010 | Dexter et al. | |
| 2011/0033436 A1 | 2/2011 | Chen et al. | |
| 2011/0053776 A1 | 3/2011 | Bahr | |
| 2012/0009238 A1 | 1/2012 | Brahm | |
| 2012/0184589 A1 | 7/2012 | Gewehr et al. | |
| 2013/0123104 A1 | 5/2013 | McKnight et al. | |
| 2013/0236522 A1 | 9/2013 | Misumi | |
| 2014/0342914 A1 | 11/2014 | Joost et al. | |
| 2015/0099626 A1 | 4/2015 | Martin | |
| 2015/0099627 A1 | 4/2015 | Martin et al. | |
| 2015/0099628 A1 | 4/2015 | Martin et al. | |

FOREIGN PATENT DOCUMENTS

| | | |
|---|---|---|
| EP | 2716748 A1 | 4/2014 |
| WO | 01/26468 | 4/2001 |
| WO | 2009/049747 A2 | 4/2009 |
| WO | 2009/091557 A1 | 7/2009 |
| WO | 2009/124707 A2 | 10/2009 |

OTHER PUBLICATIONS

Kloepper, Joseph W. et al., Induced Systemic Resistance and Promotion of Plant Growth by Bacillus spp., Pytopathology, vol. 94, No. 11, 2004, 1259-1266.
Bergey's Manual of Systematic Bacteriology, vol. 1 (1984)—voluminous.
Ashland Safety Data Sheet for Dextrol™ OC-180 dated May 21, 2015 (13 pages).
Safety Data Sheet for Rexa® 88B dated Feb. 10, 2015 (15 pages).
Safety Data Sheet for "Sokolan CP9" dated Apr. 29, 2015 (9 pages).
Product label for Ammo 2.5 EC Insecticide (Cypermethrin)dated Jul. 31, 2012 (5 pages).
Safety Data Sheet for Attaflow® FL (Attapulgite Clay) dated Aug. 7, 2014 (10 pages).
Product label for Brigade® 2EC Insecticide/Miticide (Bifenthrin) dated Oct. 2, 2012 (25 pages).
Product label for Gladiator™ insecticide/miticide (Zeta-Cypermethrin/Avermectin) dated Jul. 9, 2012 (23 pages).
Material Safety Data Sheet for Myconate HB (Formononetin)dated Sep. 8, 2009 (4 pag
Product label for Nufos® 4E insecticide (Chlorpyrifos) dated Dec. 20, 2012 (39 pages).
Extended label for Ratchet™ liquid dated Aug. 2011 (2 pages).
Safety Data Sheet for Sokalan® CP 10 dated Mar. 9, 2015 (9 pages).
Product Label for Talstar PL Granular insecticide dated Mar. 21, 2011 (3 pages).
Product Label for Zoro® Miticide/Insecticide (Abamectin) dated Mar. 29, 2012 (31 pages).
Third Party Observation submitted Mar. 30, 2016 relating to International Application No. PCT/US2014/068571 (5 pages).
Product Label for Capture® LFR™ insecticide (Bifenthrin) dated Apr. 4, 2013 (19 pages).

* cited by examineres).

*Primary Examiner* — Alton Pryor
(74) *Attorney, Agent, or Firm* — FMC Corporation

(57) ABSTRACT

Insecticidal compositions suitable for use in preparation of insecticidal liquid fertilizers are disclosed. The compositions include bifenthrin, a polymeric dispersant, a suspension agent, a freeze-thaw stabilizer, and optionally a preservative.

12 Claims, No Drawings

LIQUID-FERTILIZER READY FORMULATIONS OF BIFENTHRIN

CROSS-REFERENCE TO RELATED APPLICATIONS

This is a divisional application of U.S. patent application Ser. No. 14/217,640, filed Mar. 18, 2014, which respectively claims the benefit under 35 U.S.C. §119(e) of U.S. Provisional Application Ser. No. 61/912,259, filed Dec. 5, 2013, the disclosure of which is incorporated herein by reference in its entirety.

TECHNICAL FIELD

The presently disclosed subject matter relates to the field of agrochemical compositions and formulations. In particular, the present disclosure includes an insecticidal composition that includes bifenthrin in combination with a polymeric dispersant. Compositions include those suitable for use in the preparation of insecticidal liquid fertilizers.

BACKGROUND

To enable the efficient elimination or control of unwanted insects in combination with providing nutrients for plants to combat adverse environmental conditions (such as heat, drought, physical contact with animals, etc.) it is desirable to formulate an effective chemical insecticide for use in preparation of insecticidal liquid fertilizers. Formulations of insecticides combined with fertilizers are desirable in agricultural and related endeavors due to the multiple benefits conveyed by just one application in a single piece of equipment. One application of such a combination or formulation provides nutrients for the plant growth, while eliminating or controlling unwanted insects that can also affect the health and vitality of the desirable plants.

Mixtures containing insecticide compositions and liquid fertilizers have been practiced in the art, but problems with the physical stability of such mixtures have caused application and efficacy issues. When a traditional insecticidal composition is combined with a liquid fertilizer, particularly a high-phosphate starter fertilizer, the combined components (surfactants, viscosity modifiers, wetting agents) of both can cause accelerated physical degradation (phase separation) of the mixture. This physical degradation can occur in the mix tanks prior to application on the plants. Often this problem goes unnoticed and results in inconsistent application of both the fertilizer and insecticide, yielding inadequate efficacy of both.

SUMMARY

In one aspect, the present invention is directed to an insecticidal composition comprising a) bifenthrin; b) a polymeric dispersant; and optionally, c) a suspension agent selected from the group consisting of attapulgite clay, fumed silica and combinations thereof. Another aspect is directed to an insecticidal composition that includes a) bifenthrin; b) a polymeric dispersant; c) a suspension agent selected from attapulgite clay, fumed silica and combinations thereof; d) a freeze-thaw stabilizer; and optionally, e) a preservative.

In one embodiment, the polymeric dispersant is selected from the group consisting of polyacrylic acids, polymethacrylic acids, copolymers thereof and salts thereof. In one specific embodiment the polymeric dispersant is selected from the group consisting of polyacrylic acids and salts thereof. In one preferred embodiment the polymeric dispersant is a salt of polyacrylic acid, having an average molecular weight between about 1000 and about 100,000 Daltons. In one preferred embodiment the salt of the polyacrylic acid comprises a sodium salt. In another preferred embodiment the salt of the polyacrylic acid is a sodium salt. In one embodiment the suspension agent is present, and is fumed silica. Preferably, the insecticidal composition comprises a) about 15% to about 30% of bifenthrin; b) about 0.2% to about 20% of a polymeric dispersant; c) 0% to about 20% of a suspension agent selected from the group consisting of attapulgite clay, fumed silica and combinations thereof; d) from about 1% to about 10% of a freeze-thaw stabilizer; and e) from 0% to about 1% of a preservative, where all % are % by weight based on the total weight of all components in the composition. The composition can further comprise one or more additives selected from the group consisting of surfactants, wetting agents, anti-foam agents, preservatives and biocides. In one embodiment, the freeze-thaw stabilizer comprises ammonium sulfate. In another embodiment, the freeze-thaw stabilizer is ammonium sulfate.

Another aspect of the invention is directed to an insecticidal liquid fertilizer composition wherein the insecticidal composition further comprises a liquid fertilizer. Preferably, the liquid fertilizer is aqueous-based. In one embodiment, the liquid fertilizer is present in a concentration of about 95.0% by weight to about 99.99% by weight based on the total weight of all components in the composition. Preferably, the other components of the insecticidal liquid fertilizer composition include bifenthrin in about 0.75% to about 1.25%, and the suspension agent in about 0.05% to about 1.0%, based on the total weight of all components in the composition. In one embodiment, the polymeric dispersant is selected from the group consisting of polyacrylic acids, polymethacrylic acids, copolymers thereof and salts thereof. In one specific embodiment the polymeric dispersant is selected from the group consisting of polyacrylic acids and salts thereof. In one preferred embodiment the polymeric dispersant is a salt of polyacrylic acid, preferably a sodium salt, having an average molecular weight between about 1000 and about 100,000 Daltons. The liquid fertilizer composition can further comprise one or more additives selected from the group consisting of freeze-thaw stabilizers, surfactants, wetting agents, anti-foam agents, preservatives and biocides. In one embodiment, the freeze-thaw stabilizer is present and comprises ammonium sulfate. In another embodiment, the freeze-thaw stabilizer is ammonium sulfate.

DETAILED DESCRIPTION

In accordance with the present disclosure, it has now been found that a new insecticidal composition significantly improves physical stability when used to prepare an insecticidal liquid fertilizer. Accordingly, in one aspect, the present disclosure provides an insecticidal composition that includes bifenthrin, a polymeric dispersant, and optionally, a suspension agent selected from clays and colloidal silicas. Another aspect is directed to an insecticidal composition that includes bifenthrin; a polymeric dispersant; a suspension agent selected from attapulgite clay, fumed silica and combinations thereof; a freeze-thaw stabilizer; and optionally, a preservative.

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

The term "ambient temperature" as utilized herein shall mean any suitable temperature found in a laboratory or other working environment, and is generally not below about 15° C. nor above about 30° C.

"Dispersants", or "dispersing agents", are substances added to a suspension of solid particles, typically a colloidal suspension, to improve the separation of the particles and to decrease or prevent settling or clumping. As used herein, the term "polymeric dispersants" includes those dispersant substances having a bona fide polymeric structure. In one embodiment, the polymeric dispersants include synthetic homopolymers or copolymers. In one aspect, the polymeric dispersants in the compositions provided herein are selected from polyacrylic acids, polymethacrylic acids, other acidic polymers, particularly polymers bearing carboxylic acid ($CO_2H$) groups, copolymers thereof, salts thereof, and combinations thereof. The SOKALAN® products of BASF Corporation are representative polymeric dispersants. A preferred product is SOKALAN® PA 30 CL polyacrylic acid dispersant, which is an aqueous dispersion of a low molecular weight polyacrylic acid, fully neutralized as the sodium salt, having an average molecular weight of about 8000 Daltons. Preferably, the average molecular weight of the polymeric dispersant is between about 1000 and about 100,000 Daltons. In one embodiment the average molecular weight is from about 1000 to about 10,000 Daltons. In one embodiment the average molecular weight of the polymeric dispersant is about 8000 Daltons. Salts of the polymeric dispersant can include, without limitation, ammonium, alkylammonium, dialkylammonium, trialkylammonium, sodium, potassium, and the like. Salts can also comprise mixtures of various cations.

In one embodiment, the clay is selected from montmorillonite, attapulgite, and combinations thereof. In one embodiment, the clay has an average particle size of about 0.1 micron. The ATTAFLOW® products of BASF Corporation are representative. A preferred product is ATTAFLOW® FL, which is an aqueous suspension of attapulgite.

Colloidal silicas include, but are not limited to, fumed silicas. In one embodiment, the fumed silica is a hydrophilic fumed silica. The AERODISP® products of Evonik Industries are representative. A preferred product is AERODISP® W 7512 S, which is an aqueous dispersion of hydrophilic fumed silica. Fumed silicas form colloidal suspensions having desirable thickening, suspending and stabilizing properties in agricultural formulations.

In one aspect, the present disclosure provides an insecticidal composition that includes a) bifenthrin; b) a polymeric dispersant; and optionally, c) a suspension agent. As used herein, the term "suspension agent" also includes thickeners and/or thickening agents. Another aspect is directed to an insecticidal composition that includes a) bifenthrin; b) a polymeric dispersant; c) a suspension agent selected from the group consisting of attapulgite clay, fumed silica and combinations thereof; d) a freeze-thaw stabilizer; and optionally, e) a preservative. In one embodiment the suspension agent is selected from clays, silicas, or combinations thereof. In one embodiment, the clay includes attapulgite. In one aspect, the silica includes a fumed silica. In one embodiment, the polymeric dispersant is selected from the group consisting of polyacrylic acids, polymethacrylic acids, copolymers thereof, salts thereof, and combinations thereof. In another embodiment, the polymeric dispersant is selected from polyacrylic acids or salts thereof. In one embodiment, the polymeric dispersant includes a salt of polyacrylic acid, having an average molecular weight between about 1000 and about 100,000 Daltons. In one preferred embodiment the salt of the polyacrylic acid includes the sodium salt. The acidic functionality of the polymeric dispersant can be totally neutralized or partially neutralized as a salt.

In one preferred embodiment, the suspension agent includes fumed silica.

In one aspect, the insecticidal composition includes a) about 5% to about 40%, preferably about 10% to about 35%, more preferably about 15% to about 30%, still more preferably about 15% to about 25% of bifenthrin; b) about 0.1 to about 30%, preferably about 0.2% to about 20%, more preferably about 1% to about 15% of a polymeric dispersant; and c) 0% to about 30%, preferably about 0.1% to about 30%, more preferably about 1% to about 20%, still more preferably about 3% to about 10% of a suspension agent selected from the group consisting of attapulgite clay, fumed silica and combinations thereof; where all % are % by weight based on the total weight of all components in the composition. In one embodiment, the polymeric dispersant is present in an amount of about 11% by weight based on the total weight of all components in the composition. In one embodiment, the suspension agent is attapulgite, present in an amount of about 10% by weight based on the total weight of all components in the composition. In another embodiment, the suspension agent is fumed silica, present in an amount of about 3.5% by weight based on the total weight of all components in the composition.

Optionally, the composition further includes one or more additives selected from freeze-thaw stabilizers, surfactants, wetting agents, anti-foam agents, preservatives and biocides. In one embodiment, the surfactant is selected from anionic surfactants, alkyl d-glucopyranosides and mixtures of two or more thereof. In one embodiment, the alkyl d-glucopyranoside surfactant includes a mixture of $C_9$-$C_{11}$ alkyl d-glucopyranosides. The AGNIQUE® products of BASF Corporation are representative. A preferred product is AGNIQUE® PG9116, which is a mixture of $C_9$-$C_{11}$ alkyl d-glucopyranosides, having a degree of polymerization of about 1.6 and a hydrophilic-lipophilic balance (HLB) of about 13.1. In one embodiment, the anionic surfactant includes an alkylbenzene sulfonic acid salt, preferably a sodium salt. Representative anionic surfactants include the STEPWET® products of Stepan Corporation. A preferred product is STEPWET® DF-90, which is the sodium salt of dodecylbenzene sulfonic acid.

In one embodiment, the freeze-thaw stabilizer includes a polyalkylene glycol, preferably propylene glycol, present in an amount from about 1% to about 10% by weight, preferably about 5% to about 10% by weight of the total of all components in the composition, preferably about 9% by weight. In one embodiment, the freeze-thaw stabilizer includes ammonium sulfate (AMS), and is present in an amount from about 1% to about 10% by weight, preferably about 5% to about 10% by weight. In one embodiment, AMS is present in about 9% by weight. AMS provides additional benefits to the formulation by also serving as a fertilizer and as a density modifier for the aqueous formulation. "Freeze-thaw stabilizers" are also known as "antifreeze agents".

In an embodiment, the anti-foam agent includes an alkylcyclotetrasiloxane, preferably an octamethylcyclotetrasiloxane silicone emulsion, for example, DOW CORNING® AF Emulsion or DOWCORNING® ANTIFOAM C Emulsion (Dow Corning Corporation). When present, the anti-foam agent is present in an amount of from about 0.001% to about 1% by weight of all the components in the total formulation.

The preservative can be an isothiazolinone or a mixture of isothiazolinones, for example, KATHON® CG/ICP preservative (a mixture of 5-chloro-2-methyl-4-isothiazolin-3-one and 2-methyl-4-isothiazolin-3-one), or LEGEND® MK preservative (Rohm and Haas Corporation), or PROXEL® BR preservative (Avecia Corporation). When present, the preservative is present in an amount of from about 0.001% to about 1% by weight of the total of all components in the formulation. Preservatives include, but are not limited to, biocidal compounds, antimicrobial compounds, and the like.

In one embodiment, the present disclosure provides an insecticidal composition that includes a) bifenthrin; b) a polymeric dispersant selected from polyacrylic acids, polymethacrylic acids, copolymers thereof, salts thereof, and combinations thereof; optionally c) a suspension agent selected from attapulgite clay, fumed silica and combinations thereof; d) an anionic surfactant; and e) a freeze-thaw stabilizing agent. Another embodiment is directed to an insecticidal composition that includes a) bifenthrin; b) a polymeric dispersant selected from polyacrylic acids, polymethacrylic acids, copolymers thereof, salts thereof, and combinations thereof; c) a suspension agent selected from attapulgite clay, fumed silica and combinations thereof; d) a freeze-thaw stabilizing agent; and optionally, e) a preservative. In one embodiment, the polymeric dispersant includes a polyacrylic acid or salt thereof. In one embodiment, the anionic surfactant includes an alkylbenzene sulfonic acid salt. In one embodiment, the freeze-thaw stabilizing agent includes ammonium sulfate. In one embodiment, the suspension agent c) is absent; in another embodiment the suspension agent is present.

In one aspect, the present disclosure provides an insecticidal composition that includes a) bifenthrin; b) a polymeric dispersant selected from polyacrylic acids, polymethacrylic acids, copolymers thereof, salts thereof, and combinations thereof; c) a suspension agent selected from attapulgite clay, fumed silica, and combinations thereof; d) an anionic surfactant; e) a freeze-thaw stabilizing agent; and f) a preservative. In one embodiment, the polymeric dispersant includes a polyacrylic acid or salt thereof. In one embodiment, the anionic surfactant includes an alkylbenzene sulfonic acid salt, preferably sodium dodecylbenzene sulfonate. In one embodiment, the freeze-thaw stabilizing agent includes ammonium sulfate. In one embodiment, the preservative includes an isothiazolinone or mixture of isothiazolinones. In one embodiment, the suspension agent includes attapulgite clay; in another embodiment the suspension agent includes fumed silica.

In one aspect, the present disclosure provides an insecticidal composition that includes from about 15% to about 30% of bifenthrin, preferably from about 15% to about 25%; from about 0.2% to about 20% of at least one polymeric dispersant; and from about 1% to about 20% of a suspension agent selected from attapulgite clay, fumed silica and combinations thereof, wherein all % are % by weight based on the total weight of all components in the composition.

Another embodiment is directed to an insecticidal fertilizer composition that includes from about 0.75% to about 1.25% of bifenthrin, from about 0.1% to about 0.75% of at least one polymeric dispersant, optionally, from about 0.05% to about 1.0% of a suspension agent selected from attapulgite clay, fumed silica and combinations thereof, and from about 95% to about 99.99% of a liquid fertilizer, wherein all % are % by weight based on the total weight of all components in the composition.

The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients, commonly known as starter fertilizers that are high in phosphorus and promote rapid and vigorous root growth. Liquid fertilizers are commonly aqueous-based. As used herein, the term "aqueous-based" indicates that the predominant solvent or vehicle is water.

The present disclosure also encompasses a method of controlling unwanted insects and providing nutrients to plants, the method includes applying to an area infested with such insects and containing such plants an effective amount of a liquid fertilizer in combination with one of the compositions of this invention.

The present disclosure further encompasses a process for preparing a composition according to the present disclosure by dispersing bifenthrin in a mixture of water and at least one polymeric dispersant, and optionally a freeze-thaw stabilizing agent, an anti-foam agent and/or a preservative; wet milling the mixture to an average particle size of about 0.1 to about 10 microns, preferably about 1 to about 5 microns, and adding a suspension agent selected from attapulgite clay, fumed silica, or combinations thereof. The process can further include the step of adding the resultant mixture to a liquid fertilizer.

The compositions of the present invention are further illustrated by the examples below. These examples serve only to illustrate the invention and should not be interpreted as limiting the scope of the invention in any way, since further modifications encompassed by the disclosed invention will be apparent to those skilled in the art. All such modifications are deemed to be within the scope of the invention as defined in the present specification and claims.

EXAMPLES

Example 1

Preparation of Compositions that Include Bifenthrin

Composition 1-1: An amount of 206.8 grams of water was combined with 38.0 grams of ammonium sulfate, 2.0 grams of an anionic surfactant (STEPWET® DF 90, Stepan Company), 44.0 grams of an acrylic homopolymer (SOKALAN® PA 30 CL, BASF), 68.6 grams of bifenthrin (100 weight % active ingredient), 40.0 grams of a suspension aid (Attaflow® FL, BASF) and 0.6 grams of an isothiazolinone compound mixture (KATHON® CG/ICP, Rohm and Haas Co.) and the mixture was stirred until homogenous. This mixture was milled to a particle size of less than 7 microns.

Composition 1-2: An amount of 232.8 grams of water was combined with 38.0 grams of ammonium sulfate, 2.0 grams of an anionic surfactant (STEPWET® DF 90), 44.0 grams of an acrylic homopolymer (SOKALAN® PA 30 CL), 68.6 grams of bifenthrin (100 weight % active ingredient), 14.0 grams of fumed silica (AERODISP® W 7512 S, EVONIK Industries) and 0.6 grams of an isothiazolinone compound mixture (KATHON® CG/ICP) and the mixture was stirred until homogenous. This mixture was milled to a particle size of less than 7 microns.

Composition 1-3: An amount of 243.4 grams of water was combined with 38.0 grams of ammonium sulfate, 2.0 grams of $C_9$-$C_{11}$ alkyl d-glucopyranoside surfactant (AGNIQUE® PG9116, BASF Corporation), 44.0 grams of an acrylic homopolymer (SOKALAN® PA 30 CL), 68.6 grams of bifenthrin (100 weight % active ingredient) and 36.0 grams of propylene glycol and the mixture was stirred until homogenous. This mixture was milled to a particle size of less than 7 microns.

Composition 1-4: An amount of 249.4 grams of water was combined with 36.0 grams of ammonium sulfate, 2.0 grams of an anionic surfactant (STEPWET® DL 90), 44.0 grams of an acrylic homopolymer (SOKALAN® PA 30 CL), 68.6 grams of bifenthrin (100 weight % active ingredient, powder form) and 36.0 grams of ammonium sulfate and the mixture was stirred until homogenous. This mixture was milled to a particle size of less than 7 microns.

Example 2

Comparative Stability Study

This example sets forth stability studies that were performed on compositions prepared in accordance with the present invention.

The physical stability of Compositions of Example 1 were tested by mixing the composition with a 11% nitrogen-37% phosphorus-0% potassium aqueous-based liquid fertilizer at a 5% active ingredient ratio. A mixture of 2.5 mL of a Composition of Example 1 and 47.5 mL of 11-37-0 aqueous liquid fertilizer was placed into a glass container, the container was sealed and inverted 30 times to mix well. The mixture was poured into a 50 mL glass column to observe the mixture's physical stability. At ten minute intervals a five mL sample of the mixture was taken and analyzed by HPLC for bifenthrin concentration. The stability of each Composition was compared with that of a known formulation of bifenthrin, an Emulsifiable Concentrate (TALSTAR® 2EC, FMC Corp.) also mixed in the same aqueous liquid fertilizer. Table 1 summarizes this data.

TABLE 1

Physical stability; ppm of bifenthrin sample over time

| Composition | 0 Minutes | 10 Minutes | 20 Minutes | 30 Minutes | 40 Minutes | 50 Minutes |
|---|---|---|---|---|---|---|
| 1-1 | 2526 | 3173 | 2492 | 3001 | 4095 | 3007 |
| 1-2 | 3552 | 3664 | 4277 | 4580 | 4418 | 4841 |
| TALSTAR ® 2EC | 9427 | 7557 | 7052 | 5630 | 4270 | 2984 |

The test data above indicate that the compositions of Example 1 are homogenous throughout the test, indicating good physical stability, whereas the comparison formulation is not homogenous and has poor physical stability when mixed with high phosphorus aqueous-based liquid fertilizer.

While this invention has been described with an emphasis upon preferred embodiments, it will be obvious to those of ordinary skill in the art that variations in the preferred compositions and methods can be used and that it is intended that the invention can be practiced otherwise than as specifically described herein. Accordingly, this invention includes all modifications encompassed within the spirit and scope of the invention as defined by the claims that follow.

What is claimed is:

1. An insecticidal composition comprising:
   a) from about 5% to about 40% of bifenthrin;
   b) from about 0.1% to about 30% of a polymeric dispersant selected from the group consisting of polyacrylic acids, polymethacrylic acids, copolymers thereof, salts thereof, and combinations thereof;
   c) from about 0.1% to about 30% of a suspension agent selected from the group consisting of attapulgite clay, fumed silica, and combinations thereof,
   d) from about 1% to about 10% of a freeze-thaw stabilizer selected from the group consisting of polyalkylene glycol and ammonium sulfate, and
   e) optionally, a preservative selected from the group consisting of isothiazolinone, a mixture of isothiazolinones, biocidal compounds, and antimicrobial compounds.

2. The composition of claim 1, wherein said polymeric dispersant is selected from the group consisting of polyacrylic acids, salts thereof, and combinations thereof.

3. The composition of claim 2, wherein said salt comprises a sodium salt.

4. The composition of claim 1, wherein said suspension agent is fumed silica.

5. The composition of claim 1 further comprising a liquid fertilizer.

6. The composition of claim 5, wherein said liquid fertilizer is aqueous-based.

7. The composition of claim 1, further comprising at least one additive selected from the group consisting of surfactants, wetting agents, anti-foam agents, preservatives and biocides.

8. The composition of claim 1, wherein said freeze-thaw stabilizer comprises ammonium sulfate.

9. The composition of claim 1, wherein said polymeric dispersant comprises a salt of polyacrylic acid, having an average molecular weight between about 1000 and about 100,000 Daltons.

10. A process for preparing a homogenous composition comprising (a) dispersing from about 5% to about 40% of bifenthrin in a mixture of water and from about 0.1% to about 30% of a polymeric dispersant selected from the group consisting of polyacrylic acids, polymethacrylic acids, copolymers thereof, salts thereof, and combinations thereof, from about 1% to about 10% of a freeze-thaw stabilizer, from about 0.1% to about 30% of a suspension agent selected from the group consisting of attapulgite clay, fumed silica, and combinations thereof and optionally an anti-foam agent and/or a preservative; and (b) wet milling the mixture to an average particle size of about 0.1 to about 10 microns, wherein said freeze-thaw stabilizer is selected from the group consisting of polyalkylene glycol and ammonium sulfate, said anti-foam agent includes an alkylcyclotetrasiloxane, and said preservative is selected from the group consisting of isothiazolinone, a mixture of isothiazolinones, biocidal compounds, and antimicrobial compounds.

11. The process of claim 10, wherein the particle size ranges between about 1 to about 5 microns.

12. A method of controlling unwanted insects and providing nutrients to plants, the method comprising applying to an area infested with insects and containing such plants an effective amount of a composition according to claim 1.

* * * * *